US 6,228,634 B1

(12) United States Patent
Blumenfeld et al.

(10) Patent No.: US 6,228,634 B1
(45) Date of Patent: *May 8, 2001

(54) THERMAL CYCLING OR TEMPERATURE CONTROL DEVICE AND METHOD USING ALUMINA PLATE

(75) Inventors: Martin Blumenfeld, Minneapolis; Jonathan Chaplin, St. Paul, both of MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/389,896

(22) Filed: Sep. 3, 1999

Related U.S. Application Data

(63) Continuation of application No. PCT/US98/04041, filed on Mar. 3, 1998, which is a continuation-in-part of application No. 08/810,641, filed on Mar. 3, 1997, now Pat. No. 6,074,868.

(51) Int. Cl.$^7$ .................................................. C12M 3/02
(52) U.S. Cl. ..................... 435/286.1; 435/287.1; 435/286.2; 435/6; 435/91.1; 435/91.2; 536/23.1; 536/24.33; 536/25.3; 935/76; 935/77; 935/86
(58) Field of Search .............................. 435/286.1, 287.1, 435/286.2, 6, 91.1, 91.2; 536/23.1, 24.33, 25.3; 935/76, 77, 86

(56) References Cited

U.S. PATENT DOCUMENTS

| 4,013,038 | 3/1977 | Rogers et al. ............................ 118/5 |
| 4,043,292 | 8/1977 | Rogers et al. ............................ 118/5 |
| 4,384,193 | 5/1983 | Kledzik et al. ....................... 219/521 |
| 4,561,961 | 12/1985 | Hofmann ............................... 204/299 |
| 4,674,846 | 6/1987 | Lippman .............................. 350/536 |
| 5,455,175 | 10/1995 | Wittwer et al. ................... 435/286.1 |
| 5,475,610 | 12/1995 | Atwood et al. ..................... 364/500 |
| 5,498,392 | 3/1996 | Wilding et al. ..................... 422/68.1 |
| 5,504,007 | 4/1996 | Haynes ............................. 435/285.1 |
| 5,525,300 | 6/1996 | Danssaert et al. ..................... 422/99 |
| 5,527,510 | 6/1996 | Atwood et al. ..................... 422/104 |
| 5,538,871 | 7/1996 | Nuovo et al. ...................... 435/91.2 |
| 5,681,111 | 10/1997 | Akbar et al. ......................... 374/185 |

FOREIGN PATENT DOCUMENTS

| 0603411 | 6/1994 | (EP) . |
| WO93/19207 | 9/1993 | (WO) . |

*Primary Examiner*—W. Gary Jones
*Assistant Examiner*—Janell Taylor
(74) *Attorney, Agent, or Firm*—Westman, Champlin & Kelly; Visala C. Goswitz

(57) ABSTRACT

A thermal cycling device comprising a ceramic sample plate, and method of use thereof, is provided. The device is adapted for in situ thermal processing of biological samples on planar substrates, in particular amplification of nucleic acids. The device comprises electrical heating means attached to the ceramic sample plate, and forced air cooling means.

33 Claims, 5 Drawing Sheets

SEQUENCE LISTING

<160> NUMBER OF SEQ ID NOS: 7

<210> SEQ ID NO: 1
<211> LENGTH: 20
<212> TYPE: DNA
<213> ORGANISM: Human papillomavirus, type 16

<400> SEQUENCE: 1
caggacccac aggagcgacc                    20

<210> SEQ ID NO: 2
<211> LENGTH: 20
<212> TYPE: DNA
<213> ORGANISM: Human papillomavirus, type 16

<400> SEQUENCE: 2
ttacagctgg gtttctctac                    20

<210> SEQ ID NO: 3
<211> LENGTH: 20
<212> TYPE: DNA
<213> ORGANISM: Human papillomavirus, type 16

<400> SEQUENCE: 3
ccggtcgatg tatgtcttgt                    20

<210> SEQ ID NO: 4
<211> LENGTH: 20
<212> TYPE: DNA
<213> ORGANISM: Human papillomavirus, type 16

<400> SEQUENCE: 4

-continued

```
atcccctgtt ttttttcca                                               20

<210> SEQ ID NO: 5
<211> LENGTH: 20
<212> TYPE: DNA
<213> ORGANISM: Human papillomavirus, type 16

<400> SEQUENCE: 5
ggtacgggat gtaatggatg                                              20

<210> SEQ ID NO: 6
<211> LENGTH: 20
<212> TYPE: DNA
<213> ORGANISM: Human papillomavirus, type 16

<400> SEQUENCE: 6
ccacttccac cactatactg                                              20

<210> SEQ ID NO: 7
<211> LENGTH: 20
<212> TYPE: DNA
<213> ORGANISM: Human papillomavirus, type 16

<400> SEQUENCE: 7
aggtagaagg gcgccatgag                                              20
```

THERMAL CYCLING OR TEMPERATURE CONTROL DEVICE AND METHOD USING ALUMINA PLATE

CROSS-REFERENCE TO RELATED APPLICATION

This application is a continuation of International Patent Application No. PCT/US98/04041, filed on Mar. 3, 1998, which in turn is a continuation-in-part of U.S. patent Application Ser. No. 08/810,641, filed Mar. 3, 1997 now U.S. Pat. No. 6,074,868, both of which are incorporated herein by reference.

BACKGROUND OF THE INVENTION

The polymerase chain reaction (PCR) is a technique involving multiple cycles that results in the geometric amplification of specific polynucleotide sequences present in a test sample each time a cycle is completed. To amplify the specific nucleic acid sequences ("target sequences"), PCR reagents are combined with the test sample. These reagents include, for example, an aqueous buffer, pH 8–9 at room temperature, usually also containing approximately 0.05 M KCl; all four common nucleoside triphosphates (e.g., for DNA polymerase, the four common dNTPs: dATP, dTTP, dCTP, and dGTP) at concentrations of approximately $10^{-5}$ M to $10^{-3}$ M; a magnesium compound, usually $MgCl_2$, generally at a concentration of about 1 to 5 mM; a polynucleotide polymerase, preferably a thermostable DNA polymerase, e.g., the DNA polymerase I from *Thermus aquaticus*, at a concentration of about $10^{-10}$ to $10^{-8}$ M; and single-stranded oligonucleotide primers, preferably deoxyribo-oligonucleotides, usually 15 to 30 nucleotides in length containing base sequences which have Watson-Crick complementary to sequences preferably on each strand of the target sequence(s). Each primer is present at a concentration of about $10^{-7}$ to $10^{-5}$ M.

Initially, a reaction tube containing the test sample is heated to a temperature at which nucleic acid sequences are denatured, generally 90° C. to 100° C. Then the sample is subjected to a temperature at which oligonucleotide primers, preferably at last two oligonucleotide primers, can anneal to opposing strands of the target sequence, generally 40° C. to 75° C. The polymerase then catalyzes the incorporation of nucleoside monophosphates, beginning at the 3' end of the primer ("primer extension"), generally at 40° C. to 75° C.

The practical benefits of PCR nucleic acid amplification have been rapidly appreciated in the fields of genetics, mole biology, cellular biology, clinical chemistry, forensic science, and analytical biochemistry. For example, see Erlich (ed.) *PCR Technology,* Stockton Press (New York) (1989); Erlich et al. (eds.), *Polymerase Chain Reaction,* Cold Spring Harbor Press (Cold Spring Harbor, N.Y.) (1989); Innis et al., *PCR Protocols,* Academic Press (New York) (1990); and White et al., *Trends in Genetics* 5/6: 185–189 (1989). PCR can replace a large fraction of molecular cloning and mutagenesis operations commonly performed in bacteria, having advantages of speed, simplicity, and lower cost Furthermore, PCR permits the rapid and highly sensitive qualitative and even quantitative analysis of nucleic acid sequences.

Although one can move PCR reaction tubes manually back and forth between thermostatted baths in each temperature range, PCR most commonly is performed in an automated temperature-controlled machine, known as a "thermal cycler," in which a microprocessor is programmed to change the temperature of a heat-exchange block or bath containing reaction tubes back and forth among several specified temperatures for a specified number of cycles, holding at each temperature for a specified time, usually on the order of one-half to two minutes. The total cycle time is usually less than 10 minutes, and the total number of cycles is usually less than 40, so that a single, multi-cycle amplification, amplifying the targeted nucleic acid sequence $10^5$ to $10^{10}$ times, normally occurs in less than seven hours and often less than four hours.

PCR has also been applied to amplify specific DNA segments inside cells, without first extracting the DNA from the cells. This technique is called in situ PCR. The cells may be individual cells, or part of a tissue sample. Most often, in situ PCR is performed an cells or thin slices of tissue ("tissue sections") mounted on microscope slides. Cells which do not form tissues, such as leukocytes and many cultured cells (such as HeLa cells), are spread out upon a slide by centrifugation, producing a "cytospin" preparation. The cells or tissue usually have been fixed by treatment with formalin, or other reagents ("fixatives"), so that their morphology is preserved and recognizable after PCR and subsequent detection of the amplified nucleic acid.

To perform in situ PCR on fixed cells or tissue samples on a glass microscope slide, the slide is pretreated with an agent that inhibits or prevents the cells or tissue from being removed during the PCR process, or during the subsequent treatments for visualization of the amplified nucleic acid. For example, the surface of the slide is treated so as to covalently bond 3-aminopropyl triethoxysilane, or the surface is coated with poly(lysine) or gelatin/chrome alum. The area of the slide with the specimen is then covered with PCR reagents. The slide and reagents are then cycled 10 to 40 times between temperatures typically between about 95° C. and 68° C., but sometimes as low as 37° C., spending at least a fraction of a minute or more at each of two or three selected temperatures during each cycle.

There are several important requirements that must be met during thermal cycling for in situ PCR to be successful. One is that evaporation of water from the PCR reagents must be prevented. No more than about 5% change from optimum PCR reagent concentrations can be tolerated without resulting in lower amplification yields or less specificity. Moreover, material which inhibits the PCR should be omitted from the process. In addition, bubbles of air or dissolved gas which are released by the reagents when they are heated should not disturb the access of the liquid reagent to the entire area to be processed. Furthermore, the conditions employed during the thermal cycling or subsequent processing to visualize the amplified nucleic acid should not disrupt tissue or cell morphology and should result in uniform and reproducible results.

Thus, in situ PCR a delicate balance between two opposite requirements of PCR in a cellular preparation: the cell and subcellular (e.g., nuclear) membranes must be permeabilized sufficiently to allow externally applied PCR reagents to reach the target nucleic acid, yet must remain sufficiently intact and nonporous to retard diffusion of amplified nucleic acid out of the cells or subcellular compartments where it is synthesized. In addition, the amplified nucleic acid must be sufficiently concentrated within its compartment to give a microscopically visible signal, yet remain sufficiently dilute that it does not reanneal between the denaturation and probe-annealing steps.

Nuovo et al. (U.S. Pat. No. 5,538,871) disclose that a commercially available thermal cycler, designed to accommodate multiple small plastic microcentrifuge tubes can be modified to accommodate microscope slides. For example, it is disclosed that a single fit metal sample block can be machined to replace the top surface of a thermal cycler. It is also disclosed that the sample block can contain vertical slots in which the microscope slides are placed However, Nuovo et al. do not disclose a sample block other than a metal sample block to perform PCR on microscope slides. Moreover, Nuovo et al. do not disclose a means to detect the temperature of the microscope slide during thermal cycling.

Thus, what is needed is an improved thermal cycling device for microscope slides.

SUMMARY OF THE INVENTION

The invention provides a thermal cycling device for regulating the temperature of a substantially flat substrate, e.g., a microscope slide, a cover slip, or a nitrocellulose or nylon membrane. The thermal cycling device of the invention comprises a substantially flat ceramic, e.g., silica, alumina, silicon carbide, zirconium oxide or boron nitride, sample plate or block for holding at least two substantially flat substrates. One substrate, the control, is attached to a means for sensing the temple of the substrate. The other substrate(s) ("test" samples) comprises a biological sample, such as a tissue section, on the upper surface of the substrate. The test samples are overlaid with a volume of liquid, e.g., reagents for in situ PCR, and then the liquid is overlaid with a water impermeable barrier, e.g., a cover slip. The substrates are then thermal cycled. Preferably, the heating of the substrates occurs on an alumina sample plan, which is heated by direct thermal conductance.

The present invention outperforms currently available thermal cycling devices because it transfers heat through a ceramic sample plate that is at least 50-fold thinner than the metal, i.e., aluminum, sample plate required for thermoelectric units of the Peltier type. Thus, the invention provides a device in which a ceramic sample plate transfers heat more rapidly to a substantially flat substrate, which comprises a biological sample, than currently available thermal cycling devices. Moreover, the device of the invention measures the temperature of the substrate directly, in contrast to currently available devices which measure the temperate of the metal sample block or other heat transfer medium, or measure the temperature of the liquid on the surface of a microscope slide. Furthermore, the device of the invention is simpler in design and thus less costly to manufacture than currently available thermal cycle.

The device is preferably contained in a housing or body, which comprises a lower hollow enclosure or compartment and an upper hollow enclosure or compartment, i.e., a lid or cover. The housing preferably comprises polystyrene, polypropylene, polyethylene, or other plastics with compatible electrical and thermal conductances. The ceramic sample plate rests on the uppermost edges of the sidewalls and endwalls of, or is mounted to the inner sidewalls and/or endwalls of, the lower hollow enclosure.

In one embodiment of the invention, the sample plate comprises an alumina sample plate which has a horizontal flat upper surface dimensioned to hold at least two microscope slides with their largest dimensions oriented horizontally. For example, an alumina sample plate with dimensions of about 6.5 inches in length, about 3.5 inches in width and about 0.05 inches deep can accommodate six microscope slides, although other dimensions are within the scope of the invention. Thus, a ceramic sample plate of the invention is about 0.002–0.125 inches, preferably about 0.004–0.040 inches, and more preferably about 0.01–0.3 inches, thick.

Alternatively, the ceramic sample plate may have at least two recesses, or wells, suitable for holding individual flat substrates, e.g., a linear recess for a microscope slide, a water impermeant barrier and a volume of a vapor barrier, e.g., mineral oil, which prevents drying of the liquid film which covers the biological sample during thermal cycling.

The invention also provides a ceramic sample plate which comprises one or more substantially vertically oriented slots, which substantially and closely enclose the substantially flat substrate, e.g., a rectilinear slot for a microscope slide with its largest dimensions oriented in an approximately vertical plane. Such orientation substantially increases the number of substrates comprising biological samples which can be analyzed at one time.

The device of the invention also comprises a temperature sensor that detects the temperature of a substantially flat substrate. Preferably, the sensor is attached or affixed to the upper surface of a control flat substrate.

The device of the invention also comprises a computer-regulated conductive heating means so as to regulate the heat transfer from the ceramic sample plate to a substantially flat substrate disposed on the sample plate. The means of heating is preferably an etched foil heater, a kapton-insulated-etched foil heater, a wire wound resistive heater or a silicone rubber insulated wire wound resistive heater, affixed or attached, e.g., glued, to the lower surface of the ceramic sample plate. Preferably, the heater is electrically insulated and controlled by a relay switch.

In order to rapidly cool the sample plate, the device of the invention includes a means for cooling the sample plate. The means for cooling the sample plate comprises a means for forcing cool, i.e., ambient, air toward the means for heating the sample plate and a means for dispersing air located between the means for cooling and the means for heating. Preferably, the means for forcing cool air toward the sample plate and the means for dispersing the air are the same, i.e., an appropriately positioned fan. Preferably, the cooling means is a fan placed beneath and parallel to, or at an angle to, e.g., 90°, the heating means. Preferably, the fan is controlled by a relay switch. Optionally, a refrigerated means of cooling may be employed for lower than ambient temperatures.

Thus, once a heating cycle is completed the fan sweeps ambient temperature air across the lower surface of the heater, and sweeeps hot air out of the device. Thus, the preset invention allows heating and cooling of a sample to take place both quickly and uniformly.

The device of the invention also comprises a controller or computer. The controller or computer, e.g., a commercial microcomputer or a self-contained microprocessor, executes commands written in software so as to turn on and off the heating and cooling elements so that the biological sample on the substantially flat surface is subjected to a predetermined temperature versus time profile. These heating and cooling cycles correspond to the denaturation, annealing and elongation, steps in a PCR.

Therefore, the device of the invention is useful for temperature-sensitive manipulations of nucleic acids or proteins, or cell preparations or living cells, that are performed on microscope slides and other substantially flat substrates employed in medical diagnostics, molecular biology, and cellular biology, at temperatures that ranges from ambient to 100° C. In particular, the device is useful for in situ PCR of a biological sample present on the flat substrate, e.g., in a method to detect the presence of the nucleic acid or protein of a pathogen, such as a virus, bacterium or fungus, in a method to detect the presence of nucleic acid sequences associated with a genetic disease, nucleic acid hybridizations, e.g., Northern and Southern blot hybridizations, or in situ hybridization of nucleic acids. For a review of in situ hybridization, see Nagai et al., 1987, *Intl. J. Gyn. Path.* 6:366–379.

PCR amplified nucleic acid, or RNA or DNA that is present in a cell in an amount that is detectable without amplification, can then be detected, for example, with a radiolabeled probe. Moreover, if the biological sample comprises protein, e.g., a tissue section, the sample can also be mixed with a moiety, e.g., antibodies, which specifically bind to a cellular protein to form a complex, and the complex subsequently detected ("immunocytochemistry"). The combination of in situ PCR and immunocytochemistry can identify the presence of a specific nucleic acid sequence and a specific protein in a single cell in a biological sample.

The device of the invention is also useful to perform a ligase chain reaction (LCR), a cyclic two-step reaction. The first step in LCR is a denaturation step. The second step is a cooling step in which two sets of adjacent, complementary primers anneal to a single-stranded target DNA molecule and are ligated together by a DNA ligase enzyme. The product of ligation from one cycle serves as a template for the ligation reaction of the next cycle. LCR results in the exponential amplification of ligation products.

In one embodiment of the invention, a device is provided for subjecting a plurality of biological samples disposed on at least one substantially flat substrate to thermal cycling. The device preferably comprises:

a thermal sensing means placed on the upper surface of one substantially flat substrate and at least one substantially flat substrate lacking said thermal sensing means and comprising at least one biological sample;

a means for holding the plurality of substantially flat substrates, wherein the means for holding comprises a ceramic sample plate, and wherein the substantially flat substrates are disposed on the upper surface of said holding means;

a means for heating the lower surface of the means for holding, wherein the means for heating is positioned parallel to and in close proximity to the means for holding;

a means for cooling the lower surface of the means for heating, wherein the means for cooling comprises a rotating means for dispersing air beneath the means for heating; and a means for controlling, wherein the controlling means is operatively connected to the means for thermal sensing, the means for heating and the means for cooling such that the temperature of the substrates can be rapidly and controllably increased and decreased by the control means in response to the temperature sensed by the means for sensing such that the biological sample can be subjected to rapid thermal cycling over a temperature range of at least 40° C.

In one embodiment of the invention, the means for heating the lower surface of the means for holding can include a plate which is positioned parallel to and in close proximity to the means for holding. For example, the heating means can include an etched foil heater that is attached to the surface of the parallel plate. The heater is attached to the surface of the parallel plate which is more distal to the sample plate. Preferably, the plate is positioned so that it is no more than about ⅛ of an inch from the ceramic plate. Preferred materials from which to form the parallel plate include ceramic, e.g., alumina, as well as metals such as aluminum and copper, although other conductive materials are also envisioned. More preferably, the parallel plate is formed from alumina. The space between the parallel plate and the sample plate is preferably filled with air. The position of the two plates relative to each other is maintained by a structure such as a gasket, e.g., formed from rubber, or by attachment of each plate to the housing. The use of two plates provides a more uniform temperature distribution across the ceramic plate.

Another preferred embodiment of the invention is a thermal cycling device useful for the amplification of nucleic acids. The device preferably comprises:

a thermal sensing means placed on the upper surface of one substantially flat substrate and at least one substantially flat substrate lacking said thermal sensing means and comprising at least one biological sample;

a means for holding the plurality of substantially flat substrates, wherein the means for holding comprises an alumina sample plate, and wherein the substantially flat substrates are disposed on the upper surface of said holding means;

a means for hating the lower surface of the means for holding, wherein the means for heating is attached to the means for holding;

a means for cooling the lower surface of the means for heating, wherein the means for cooling comprises a rotating means for dispersing air beneath the means for heating; and a means for controlling, wherein the controlling means is operatively connected to the means for thermal sensing, the means for heating an the means for cooling such that the temperature of the substrates can be rapidly and controllably increased and decreased by the control means in response to the temperature sensed by the means for sensing such that the biological sample can be subjected to rapid thermal cycling over a temperature range of at least 30° C.

Further provided is a device for maintaining the temperature of a plurality of biological samples which are disposed on at least one substantially flat substrate. The device comprises:

a thermal sensing means placed on the surface of one substantially flat substrate and at least one substantially flat substrate lacking said thermal sensing means and comprising at least one biological sample;

a means for holding the plurality of substantially flat substrates, wherein the means for holding comprises a ceramic sample plate, and wherein the substantially flat substrates are disposed on the surface of said holding means;

a means for healing the surface of the means for holding, wherein the means for heating is positioned in close proximity to the means for holding;

a means for cooling the surface of the means for heating, wherein the means for cooling comprises a rotating means for dispersing air, and a means for controlling, wherein the controlling means is operatively connected to the means for thermal sensing, the means for heating and the means for cooling such that the temperature of the substrates can be maintained at a particular temperature by the control means in response to the temperature set by the means for sensing such that the biological sample can be maintained at a particular temperature over a temperature range of at least 40° C.

In one embodiment of the invention, the substantially flat substrate is a nylon or nitrocellulose membrane comprising isolated nucleic acid The membrane is contacted with an amount of a labeled probe and a hybridization solution to form a mixture. Preferably, the mixture is placed in a water impermeable vessel or container, e.g., a plastic bag that can be sealed. The mixture is then maintained at a particular temperature by placing the mixture on the ceramic sample plate. The temperature is selected so as to permit Watson Crick base pairs to be formed between the probe and a target nucleic acid sequence present in the isolated nucleic acid, i.e., Northern or Southern hybridization. The vessel or container is then overlaid with a flat substrate having width and lengthwise dimensions similar to or greater than those of the vessel, i.e., the vessel is sandwiched between the sample plate and the flat substrate.

Also provided is a device useful for the in situ hybridization of nucleic acids. The device comprises:

a thermal sensing means placed on the surface of one substantially flat substrate and at least one substantially flat substrate lacing said thermal sensing means and comprising at least one biological sample;

a means for holding the plurality of substantially flat substrates, wherein the means for holding comprises an alumina sample plate, and wherein the substantially flat substrates are disposed on the surface of said holding means;

a means for heating the lower surface of the means for holding, wherein the means for heating is attached to the means for holding;

a means for cooling the lower surface of the means for heating, wherein the means for cooling comprises a rotating means for dispersing air; and a means for controlling, wherein the controlling means is operatively connected to the means for thermal sensing, the means for heating and the means for cooling such that the temperature of the substrates can be maintained at a particular temperature by the control means in response to the temperature sensed by the means for sensing such that the biological sample can be maintained at a particular temperature over a temperature range of at least 30° C.

The invention also provides a device for subjecting a biological sample to thermal cycling. The device comprises:

a housing;

a flat substrate having a thermal sensor coupled to said flat substrate, said flat substrate having a biological samples disposed thereon;

a holder for said flat substrate, said holder attached to said housing, wherein said holder comprises a ceramic sample plate, and wherein said flat substrate is disposed on the upper surface of said ceramic sample plate;

a cooler for said flat substrate, said cooler attached to said housing; and a heater thermally coupled to said flat substrate.

Also provided is a device for maintaining the temperature of a biological sample. The device comprises:

a housing;

a flat substrate having a thermal sensor coupled to said flat substrate, said flat substrate having a biological samples disposed thereon;

a holder for said flat substrate, said holder attached to said housing, wherein said holder comprises a ceramic sample plate, and wherein said flat substrate is disposed on the upper surface of said ceramic sample plate;

a cooler for said flat substrate, said cooler attached to said housing; and a heater thermally coupled to said flat substrate.

Yet another embodiment of the invention

The invention also provides a method for thermal cycling, or maintaining the temperature of; a biological sample on a substantially flat surface. One embodiment of the invention comprises a method for amplifying target nucleic acid. The method comprises:

(a) contacting a biological sample, which comprises nucleic acid, that is disposed on a substantially flat substrate with an amount of PCR reagents so as to yield a mixture;

(b) subjecting the mixture to thermal cycling in the device of the present invention so as to yield amplified nucleic acid.

Also provided is a method for in situ PCR amplification of target nucleic acid wherein said amplified nucleic acid is spatially confined to individual cells originally containing said target nucleic acid. The method comprises (a) contacting fixed cells suspected of containing the target nucleic acid with an amount of PCR reagents sufficient to amplify said target nucleic acid so as to form a mixture; and (b) subjecting the mixture to thermal cycling in the device of the present invention so as to yield amplified nucleic acid.

Further provided is a method for in situ hybridization of a target nucleic acid wherein said target nucleic acid is spatially confined to a substantially flat surface. The method comprises:

(a) contacting the target nucleic acid with an amount of a labeled probe comprising a preselected DNA comprising the target nucleic acid sequence to as to form a mixture;

(b) maintaining the temperature of the mixture for a sufficient time to form binary complexes between at least a portion of said probe and said target nucleic acid, wherein the temperature is maintained on the device of the present invention; and (c) detecting the absence or presence of said binary complexes.

Yet another embodiment of the invention is a method for in situ hybridization of target nucleic acid wherein said target nucleic acid is spatially confined to individual cells originally containing said target nucleic acid. The method comprises:

(a) contacting fixed cells suspected of containing the target nucleic acid with with an amount of a labeled probe comprising a preselected DNA comprising the target nucleic acid sequence so as to form a mixture; and (b) maintaining the temperature of the mixture for a sufficient time to form binary complexes between at least a portion of said probe and said target nucleic acid, wherein the temperature is maintained on the device of the invention; and (c) detecting the absence or presence of said binary complexes.

DETAILED DESCRIPTION OF THE INVENTION

Figure 1:
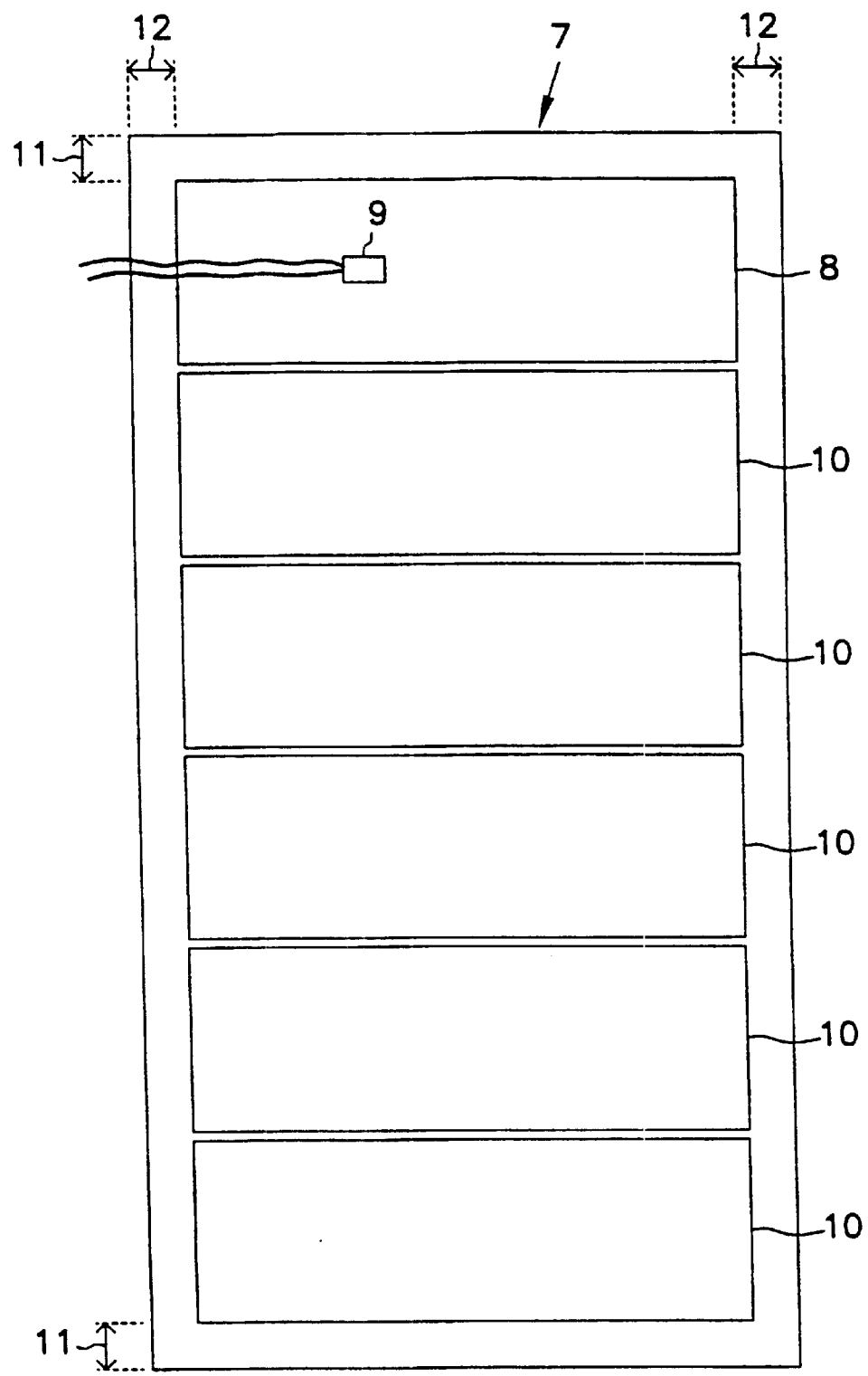
FIG. 1 is a top view of a rectilinear ceramic sample plate 7, a microscope slide 8 fitted with a temperature sensor 9, and an array of experimental slides 10. The endwall margins 11 and the sidewall margins 12 of the sample plate provide support for a lid, which covers the sample plate 7 and slides. In this embodiment, the ceramic sample plate 7 is 6.5" long and 3.5" wide, Since standard microscope slides are 3" long and 1" wide, the illustrated sample plate accommodates the slide with a temperature sensor 9, and five experimental slides 10.

The invention provides a thermal cycling device comprising a ceramic sample plate or block. The ceramic sample plate increases the speed and reliability of in situ PCR performed on a biological sample attached to a substantially flat substrate. The invention is an improvement over commercially available thermal cycling devices as the sample plate of the invention accelerates and renders more uniform the heat transfer which occurs during thermal cycling.

Definitions

As used herein, a "substantially flat substrate" means a material on which isolated nucleic acid, polypeptide or protein, or intact cells or tissues, can be maintained for an indefinite period of time. Thus, materials such as plastic, glass, nitrocellulose, nylon and the like are substantially flat substrates within the scope of the invention. Plastics useful as substrates include, but are not limited to, polystyrene, polypropylene, polycarbonate, polyethylene and the like.

As used herein, the term "biological sample" includes isolated and/or purified nucleic acid or polypeptide, or intact cells present in a specimen or sample obtained from any prokaryotic or eukaryotic organism, e.g., blood or a biopsy sample from a mammal. More than one biological sample may be present on any one substantially flat substrate. A preferred biological sample is a mammalian tissue section. As used herein, the teams "isolated and/or purified" refer to in vitro isolation of a nucleic acid or polypeptide molecule from its natural cellular environment, and from association with other components of the cell, such as nucleic acid or protein.

As used herein, the term "ceramic" means a compression-resistant, heat-resistant, corrosion-resistant substance prepared by firing terrestrial minerals such as clay, corundum and the like, which comprise one or more metals in combination with a non-metal, generally oxygen. Ceramics within the scope of the invention include, silica, alumina, silicon carbide, zirconium oxide and boron nitride. Alumina is a preferred ceramic for use in the devices and methods of the invention, as alumina conducts heat more efficiently than other ceramics.

"PCR" refers to a process of amplifying one or more specific nucleic acid sequences, wherein 1) oligonucleotide primers which determine the ends of the sequences to be amplified are annealed to single-stranded nucleic acid in a test sample, 2) a nucleic acid polymerase extends the 3' cads of the annealed primers to create a nucleic acid stand complementary in sequence to the nucleic acid to which the primers were annealed, 3) the resulting double-stranded nucleic acid is denatured to yield two single-stranded nucleic acids, and 4) the processes of primer annealing, primer extension, and product denaturation are repeated enough times to generate easily identified and measured amounts of the sequences defined by the primers Practical control of the sequential annealing, extension, and de on steps is exerted by varying the temperature of the reaction container, normally in a repeating cyclical manner. Annealing and extension occur optimally in about the 35° C. to 80° C., preferably about the 40° C. to 75° C., temperature range, whereas denaturation requires temperatures in about the 80° C. to 100° C. range.

While a single primer pair is most often employed in PCR, a single primer ("one-sided PCR"), multiple primers ("multiplex PCR"), degenerate primers, and nested primers may also be employed in the methods of the invention. Moreover, in addition to amplification of DNA, the device and method of the invention can be employed for RT-PCR, i.e., reverse transcription of an RNA molecule to produce a single stranded cDNA with subsequent PCR of the cDNA.

PCR specificity may be increased by omitting at least one reagent necessary for PCR until the sample temperature is between 50–80° C. ("Hot Start™"), the addition of a reagent which interferes with nonspecific polymerase reactions (e.g., SSB), or the addition of a modified nucleotide (e.g., dUTP) and the corresponding glycosylase (e.g., UNG) into the reaction mixture. See U.S. Pat. No. 5,538,871, the disclosure of which is incorporated by reference herein.

"Thermal cycling" commonly is automated by a "thermal cycler," an instrument which rapidly (on the time scale of one to several minutes) heats and cools a "sample compartment," a partly or completely enclosed container holding the vessel, e.g., a microcentrifuge tube, or flat substrate, a microscope slide, on which nucleic acid amplification occurs and the heat-transfer medium directly contacting the PCR vessel or flat substrate. Most commonly, the sample compartment is a "sample block," which can be temperature controlled. While conventional sample blocks are manufactured from metal and contain wells designed to fit tightly the plastic microcentrifuge tubes in which PCR amplification normally is performed, the sample plate of the present invention is manufactured from ceramic, preferably alumina, and replaces some or all of the conical wells in conventional thermal cyclers with a flat surface or slots designed to optimize heating and cooling of a biological sample, preferably a sample on a flat substrate, e.g., a tissue section on a microscope slide, although it is envisioned that a ceramic sample plate of the invention may be manufactured to hold or support other shaped vessels, e.g., microcentrifuge tubes.

"PCR reagents" refers to the chemicals, apart from the biological sample, needed to make nucleic acid amplification work. The reagents consist of five classes of components: (1) an aqueous buffer, (2) a water-soluble magnesium salt, (3) at least four deoxyribonucleoside triphosphates (dNTPs), although these can be augmented or sometimes replaced by dNTPs containing base analogues which Watson-Crick base-pair like the conventional four bases, such as the analog deoxyuridine triphosphate (dUTP) and dUTP carrying molecular tags such as biotin and digoxigenin, covalently attached to the uracil base via spacer arms, (4) oligonucleotide primers (normally two for each target sequence, with sequences which define the 5' ends of the two complementary stands of the double-stranded target sequence), and (5) a polynucleotide polymerase, preferably a DNA polymerase, most preferably a thermostable DNA polymerase, which can tolerate temperate between 90° C. and 100° C. for a total elapsed time of at least 10 minutes without losing more than about half of its activity.

"Southern analysis" or "Southern blotting" is a method by which the presence of DNA sequences in a restriction endonuclease digest of DNA or DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe, i.e., "Southern hybridization," as described in sections 9.37–9.52 of Sambrook et al., supra.

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as 3, by biotinylation or with an enzyme. The RNA to be analyzed can be usually electrophoretically separated on an agarose or polyacrylamide gel, transferred to nitrocellulose, nylon, or other suitable membrane, and hybridized with the probe, i.e., "Northern hybridization," using standard techniques well known in the art such as those described in sections 7.39–7.52 of Sambrook et al., supra.

"Fixed cells" refers to a sample of cells which has been chemically treated to strengthen cellular structures, particularly membranes against disruption by solvent changes, temperature changes, mechanical stresses, and drying. Cells may be fixed either in suspension or while contained in a sample of tissue, such as might be obtained during autopsy, biopsy, or surgery. Cell fixatives generally are chemicals which crosslink the protein constituents of cellular structures, most commonly by reacting with protein amino groups. Preferred fixatives are buffered formalin, 95% ethanol, formaldehyde, paraformaldehyde, or glutaraldehyde. Fixed cells also may be treated with protein enzymes which digest proteins, or with surfactants or organic solvents which dissolve membrane lipids, in order to increase the permeability of fixed cell membranes to PCR reagents. Such treatments must follow fixation to assure that membrane structures do not completely fall apart when the lipids are removed or the proteins are partially cleaved. Protease treatment is preferred following fixation for more than one hour and is less preferred following shorter fixation intervals. For example, a ten minute fixation in buffered formalin, without protease treatment, is after suspended cells (e.g., from blood) have been deposited centrifugally on a slide by cytospin procedures standard in the cytochemical art.

A preferred mode of fixing cell samples for in situ PCR according to the present invention is to incubate them in 10% formalin, 0.1 M Na phosphate, pH 7.0, for a period of 10 minutes to 24 hours at room temperature. The cells may be a suspension, as would be obtained from blood or a blood fraction such as buffs coat, or may be a solid tissue, as would be obtained from biopsy, autopsy, or surgical procedures well known in the art of clinical pathology. If PCR is to be performed in cell suspension, suspended cells preferably are centrifuged after formalin fixation, resuspended in phosphate-buffered saline, and re-centrifuged to remove the fixative. The washed, pelleted cells may be resuspended in PCR buffer and added directly to a PCR tube. If PCR is to be performed on a microscope slide, suspended cells preferably are deposited on the slide by cytospin, fixed 10 minutes in buffered formalin, washed 1 minute in water, and washed 1 minute in 95% ethanol. Alternatively, suspended cells can be pelleted in a centrifuge tube and the pellet can be embedded in paraffin and treated like a tissue specimen. Tissue samples may be processed further and then embedded in paraffin and reduced to serial 4–5 $\mu$m sections by microtome procedures standard in the art of clinical pathology. Histochemical sections are placed directly on a microscope slide. In either case, the slide preferably will have been treated with 2% 3-aminopropyltriethoxysilane in acetone and air dried. After smears or sections have been applied to slides, the slides are heated at about 60° C. for about 1 hour. Paraffin-embedded sections can be deparaffinized by 2 serial 5 minute washes in xylene and 2 serial 5 minute washes in 100% ethanol, all washes occurring at room temperature with gentle agitation.

"Histochemical section" refers to a solid sample of biological tissue which has been frozen or chemically fixed and hardened by embedding in a wax or a plastic, sliced into a thin sheet, generally several microns thick, and attached to a microscope slide.

"Cytochemical smear" refers to a suspension of cells, such as blood cells, which has been chemically fixed and attached to a microscope slide.

"Vapor barrier" refers to an organic material in which water is insoluble, which covers a PCR reaction or preparation in a way which substantially reduces water loss to the atmosphere during thermal cycling. Preferred vapor barrier materials are liquid hydrocarbons such as mineral oil, or paraffin oil, although some synthetic organic polymers, such as fluorocarbons and silicon rubber, also may serve as effective PCR vapor barriers. Waxes which are solid at temperatures below about 50° C. and liquid at higher temperatures also make convenient vapor barriers.

To isolate the PCR reagents from the atmosphere and from the vapor barrier, a thin, "water-impermeant barrier" such as a plastic or glass film, e.g., a glass cover slip or a polypropylene cover slip, is placed over the liquid film which comprises the PCR reagents. The water-impermeant barrier is generally attached to the microscope slide. For example, a cover slip can be placed over the liquid film and sealed to the microscope slide with nail polish or a similar adhesive. See Komminoth et al., *Diagnostic Molecular Pathology,* 1(2), 85–9(1992). The cover slip can also be clipped to the slide. See U.S. Pat. No. 5,527,510. Alternatively, a gasket can be placed between the cover slip and a chambered slide, which contains the PCR reagent, sealed with 2.5% hot agarose and the assembly covered with saran wrap. See, Chiu et al., *Histochem. and Cytochem.,* 40, 333–341 (1992). However, any other fastening mechanism may be employed to attach the cover slip to a microscope slide, such as the use of other high temperature resistant adhesives.

"Detection" of PCR-amplified nucleic acid refers to the process of observing, locating, or quantitating an analytical signal which is inferred to be specifically associated with the product of PCR amplification, as distinguished from PCR reactants. The analytical signal can result from visible or ultraviolet absorbance or fluorescence, chemiluminescence, or the photographic or autoradiographic image of absorbance, fluorescence, chemiluminescence, or ionizing radiation. Detection of in situ PCR products involves microscopic observation or recording of such signals. The signal derives directly or indirectly from a molecular "tag" attached to a PCR primer or dNTP or to a nucleic acid probe, which tag may be a radioactive atom, a chromophore, a fluorophore, a chemiluminescent reagent, an enzyme capable of generating a colored, fluorescent, or chemiluminescent product, or a binding moiety capable of reaction with another molecule or particle which directly carries or catalytically generates the analytical signal. Common binding moieties are biotin, which binds tightly to streptavidin or avidin, digoxigenin, which binds tightly to anti-digoxigenin antibodies, and fluorescein, which binds tightly to anti-fluorescein antibodies. The avidin, streptavidin, and antibodies are easily attached to chromophores, fluorophores, radioactive atoms, and enzymes capable of generating colored fluorescent, or chemiluminescent signals.

"Nucleic acid probe" refers to an oligonucleotide or polynucleotide containing a sequence complementary to part or all of the PCR target sequence, also containing a tag which can be used to locate cells in an in situ PCR preparation which retains the tag after mixing with nucleic acid probe under solvent and temperature conditions which promote probe annealing to specifically amplified nucleic acid.

Device of the Invention

The invention provides a thermal cycler comprising a ceramic sample plate which is optimized for heat flow to and from biological samples attached or affixed to a substantially flat substrate, e.g., a microscope slide, present on the upper surface of the sample plate. For in situ PCR applications where very few slides are to be run simultaneously, the top surface is designed to create flat horizontal areas large enough to hold slides so that the large dimensions (height and width) are horizontal. These flat areas may be recessed in shallow wells, which may optionally hold a vapor barrier that covers the slides, or which physically isolate one substrate from another. For microscope slides, the area is at least about 16 mm wide and 77 mm long to fit conventional glass microscope slides. The wells are at least about 2 mm deep to fit a slide and cover slip and optionally a vapor barrier.

For in situ PCR applications where a large number of samples each affixed to a substantially flat substrate such as a microscope slide are to be run simultaneously, the ceramic sample plate may be designed to contain many narrow, deep, vertical or approximately vertical slots, sized to hold slides inserted edgewise with minimal space separating the slide from the ceramic surfaces facing the top and bottom sees of the slide. The intervening space normally is filled with mineral oil or another nonvolatile liquid to provide a vapor barrier and efficient heat transfer during thermal cycling. However, because the heat transfer between a flat sample plate and a flat substrate is more efficient, a vapor barrier may be optional for some applications. The plane of a slot may be inclined from the vertical by as much as about 45° in order to use the force of gravity to assure that one surface of the slide touches the ceramic of the sample plate. Slots must be about 15 mm deep, at least 77 mm long, and at least 2 mm wide to fit a conventional slide plus a cover slip. This design is not compatible with manual addition of missing PCR reagent(s) because it blocks rapid access to the in situ PCR preparation for cover slip removal, manual addition of the missing PCR reagent(s), and cover slip replacement The ceramic sample plate 7 can include both wells optimized for biological samples present on a substantially flat substrate, e.g., a microscope slide, and wells designed to hold conventional nucleic acid amplification reaction tubes, e.g., 0.5 ml microcentrifuge tubes. Preferably, the reaction tube wells occupy one or several rows along the edges of the sample plate, reserving the central area of the sample plate for microscope slide wells.

It is also envisioned that the ceramic sample plate of the invention may be prepared so as to replace the top surface of a sample plate present in a commercially available thermal cycler, leaving the other design features (except possibly plate or block thickness) substantially unchanged in order to minimize the impact of the invention on thermal cycler manufacture and performance. It is also envisioned that the ceramic sample plate of the invention is equal in mass to the conventional sample block of a commercially available thermal cycler, to minimize impact on heating and cooling kinetics.

To prepare a ceramic sample plate 7, the sample plate may be manufactured by machining a single ceramic plate, for example with a rotary mill, exact dimensions, wells, and other contours needed to integrate with the rest of the thermal cycler. Holes for bolting the plate to the rest of the thermal cycler may be made with a drill press. The rectilinear shape of wells adapted to fit microscope slides may also be produced by stamping or machining of relatively thin sheets of ceramic which are bolted together to create a laminated assembly. The entire plate may be laminated; or just the top portion, holding the microscope slide wells, can be laminated and bolted to a solid bottom portion which contains the features of the plate which integrate with the rest of the thermal cycler.

The device of the invention 21 is preferably enclosed in a housing or body which comprises a lower hollow compartment 16 and an upper hollow compartment (the lid; 9). Although the two compartments 9 and 16 may be formed in any suitable, compatible and practical shape, they are preferably box-shaped Each compartment comprises a pair of sidewalls 20a and 20b and a pair of endwalls 21a and 21b. The lid 15 also comprises a substantially flat upper surface 24 attached to the sidewalls and endwalls of the lid. The lower compartment 16 comprises a substantially flat lower surface 25 the outer surface on which, preferably, are feet. The lower surface 25 comprises an inlet opening 18 for ambient air intake. The lower surface 25 of the lower compartment is attached to the sidewalls 20a and 20b and endwalls 21a and 21b of the lower compartment 16. The sidewalls 20a and 20b and/or endwalls 21a and 21b of the lower compartment 16 have at least one outlet opening 19.

The housing may be fabricated from any available material, e.g., a plastic, metal such as stainless steel, ceramic, glass or combinations of any of the foregoing materials. However, it is preferred that the material be plastic, such as polypropylene or polycarbonate or the like, so that the housing may be molded in an inexpensive fashion. Moreover, it is preferred that the walls of the housing, including sidewalls 20a and 20b, endwalls 21a and 21b, lower surface 24, and upper surface 25, be relatively thin in dimension in order to provide a housing with low thermal mass: The most straightforward, but not necessarily limitative, construction of housing is one in which all of the walls are of the same relative thickness.

The lower compartment 16 comprises a ceramic sample plate 7, which provides mechanical support and a heat exchange element for the flat substrates. Preferably, the ceramic sample plate comprises alumina (Hoechst Ceramic North America Inc., Mansfield, Mass., Coors Ceramics Co., Golden, Colo.) The outer margins of the sample plate 5 and 6 may lie on the outer and uppermost margins of the lower compartment 16, or may be affixed mounted or attached to the inner sidewalls 20a and 20b and endwalls 21a and 21b of the lower compartment 16 by, for example, a support bracket. The ceramic sample plate 7 may be substantially flat, or may comprise a plurality of recessed rectilinear wells for microscope slides. It is preferred that the wells in the sample plate may include sidewalls which are integrally formed in, and from the same material as, the ceramic sample plate 7. Moreover, the wells are preferably configured to hold the slides, or other substantially flat substrate, in relatively tight contact with sidewalls of the wells, to facilitate optimum conduction of heat to and from the slides.

Reference is now made to the drawings, which describe preferred embodiments of the invention, but are not intended to limit the invention to the embodiments shown. As shown in FIG. 1, a ceramic sample plate 7, preferably an alumina sample plate, is dimensioned so as to accommodate 6 microscope slides. However, the ceramic sample plate may be fashioned so as to accommodate fewer or greater than 6 substantially flat substrates. The upper surface of one representative substantially flat substrate, e.g., a microscope slide 8, is attached to a thermosensor 9. The other substantially flat substrates 4 each comprise at least one biological sample on their upper surface. The outer edges or margins of the surface of the ceramic sample plate 5 and 6 are useful for placing the lower edges of a lid 15 over the slides during thermal cycling.

The thermosensor 9 is an integrated circuit which provides an output current that is directly proportional to temperature (K°) (AD592 or AD590 from Analog Devices, Norwood, Mass.). The thermosensor 9 thus provides an electrical input signal to the microcomputer or microprocessor 23 which corresponds to the temperature of the representative substantially flat substrate 2 on the sample plate 7. Temperature monitoring during onion of the thermal cycling device of the present invention is preferably achieved using a type K thermocouple (COI-K; Omega Engineering, Inc., Stamford, Conn.) or a 100Ω resistance temperature device (F3101; Omega Engineering, Inc., Stamford, Conn.). The controller uses this information to regulate the heating means 9 and cooling means 11 according to predetermined temperature versus time profiles programmed therein.

Figure 2:
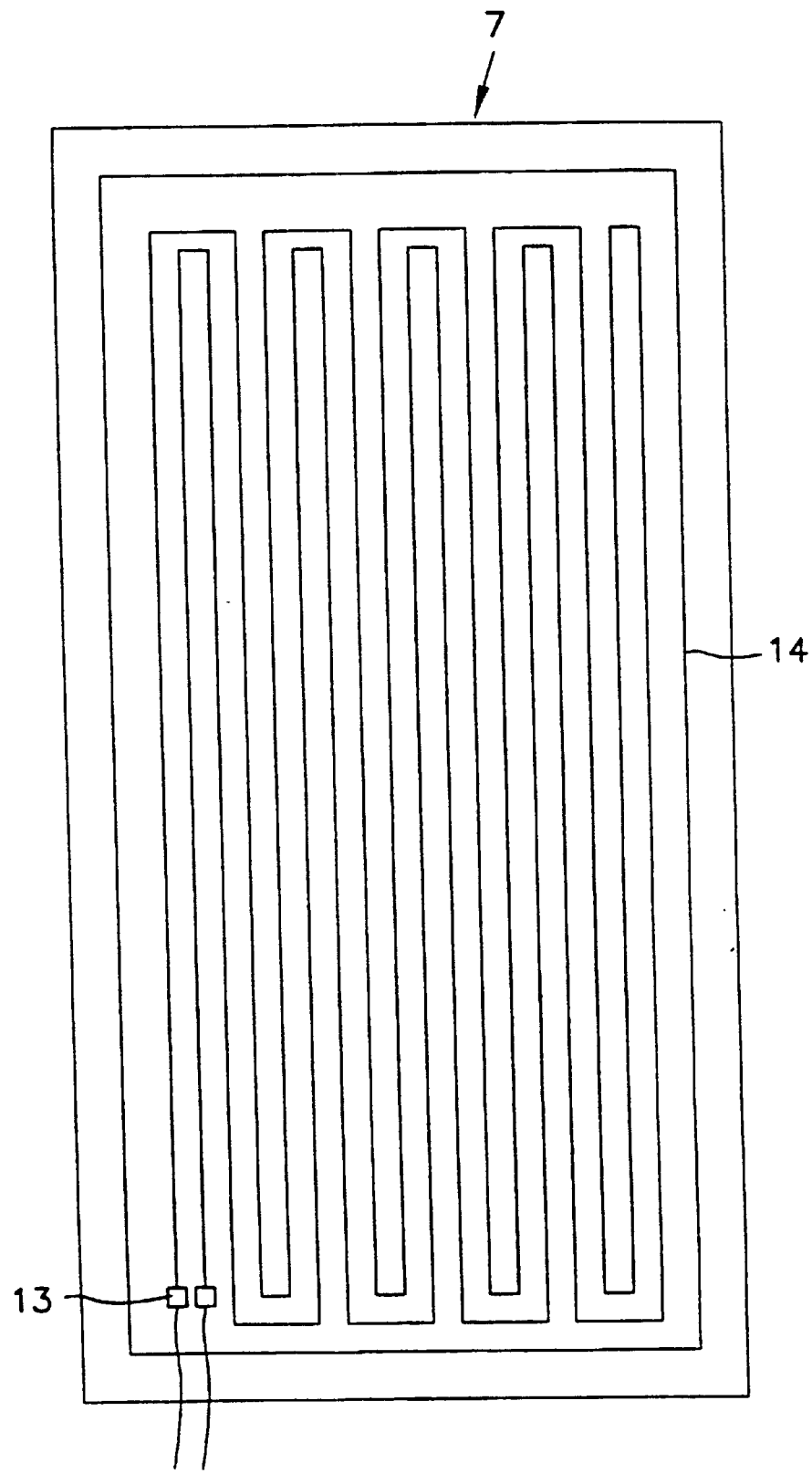
FIG. 2 is a bottom view of the ceramic sample plate 7 to which a 6" long×3" wide etched-foil heater 14 is attached. A solder pad connection 13 is attached to the lower surface of the beater.

FIG. 2 illustrates an exemplary heating means 14 for the ceramic sample plate 7. The heating means is preferably an etched foil type heater (HK 5468 R93.8 L12A; MINCO Products, Minneapolis, Minn.) which is preferably glued to the ceramic sample plate 7. However, any heating unit suitable for heating the ceramic sample plate may be used. The heating means is activated by an output relay 13 attached to the microcomputer or microprocessor 23. Preferably, the relay is Crydom A1202 purchased from Allied Electronics, Fort Worth, Tex.).

Figure 3:
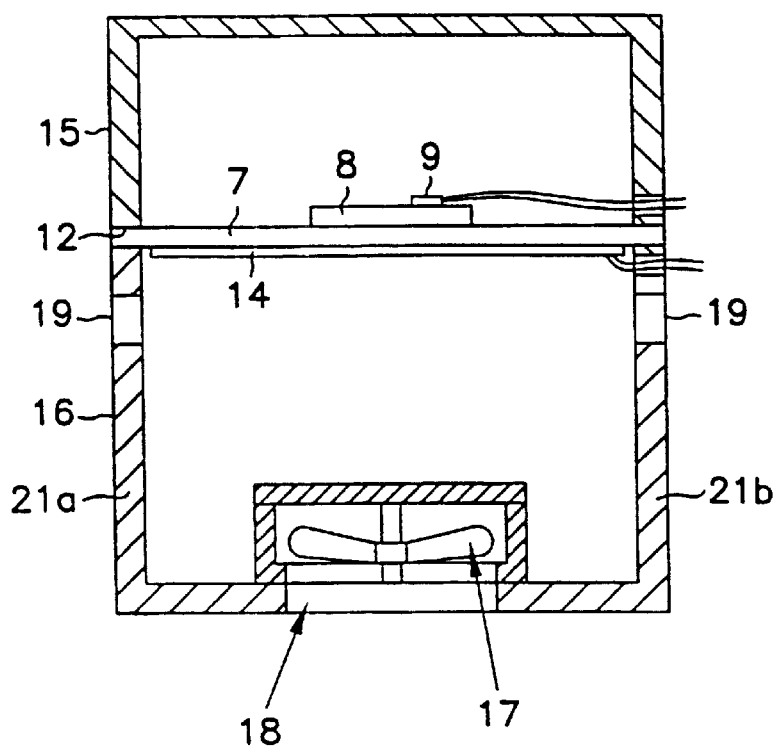
FIG. 3 illustrates a cross sectional view of a fan mounting arrangement in which the impeller blades of a fan 17 are parallel to the ceramic sample plate 7. Air is drawn into the lower compartment 16 through input openings or vents 18 and driven against the heater by the fan, and out of the lower compartment 16 through vents 19 in the endwalls 21a and 21b located perpendicular to and between the fan 17 and the heater 14. Also shown are the lid 15 and outlet openings or vents 19.

FIG. 3 illustrates a side view of the thermal cycling device of the invention. The lid 9 can be opened to allow access to the ceramic sample plate 7. To cool the ceramic sample plate 7, the heating means 9 is deactivated and the fan 17 is activated Air from outside the housing is drawn into the lower compartment 16 though an inlet opening 18 by the fan 17 which is connected to a motor shaft driven by a motor (not shown). The fan 17 is mounted to the interior surface of the lower wall of the lower compartment, although other mounting arrangements are envisioned The lower surface has a inlet opening 18. There is at least one other opening 19 in the sidewall 20a or 20b or the endwall 21a or 21b of the lower compartment 16. Thus, the present invention may have two such openings, but the present invention is not limited to two since the number of openings may vary, depending upon the design and configuration of the housing. These openings provide communication between interior of the housing and the outside environment, so that air may be moved into and out of the hollow interior of the lower compartment, according to the present invention.

The fan assembly preferably employs a propeller type fan due to its generally low thermal mass, or if desired, a squirrel cage type fan, the fan preferably having at least about 40, more preferably at least about 50, and even more preferably at least about 60 cubic feet per minute minimum capacity. The fan 17 draws ambient temperature air through the inlet opening 18 into the hollow interior of the lower compartment, and forces the air against the heating means 14. The air is dispersed through outlet or exit openings 19 in the endwall or sidewalls of the lower compartment. Operation of the fan 17 allows the sample plate 7 in to be brought to a lower predetermined temperature as quickly as possible. Thus, due to the minimum thermal mass of the sample plate 7, and the action of the fan 17, vast quantities of air are forced against the heating means 14 and from there out of the hollow interior of the outlet openings 19 in the lower compartment 16. Thus, rapid cooling of substantially flat substrates on the sample plate is obtained. Moreover, the combination of heating and cooling means together allow the flat substrates to be maintained at a particular temperature.

The fan motor (not shown) is located externally of housing. It would be disadvantageous to mount the motor within the chamber which would subject the motor to temperature variations and also would add the thermal mass of the motor to that which is subject to heating and cooling. For example, a Comair FT12M3 fan purchased from Digi-Key Corporation (Thief River Falls, Minn.;) can be employed in the device of the invention, although other cooling devices and fins well known to the art may be employed in the practice of the invention.

Figure 4:
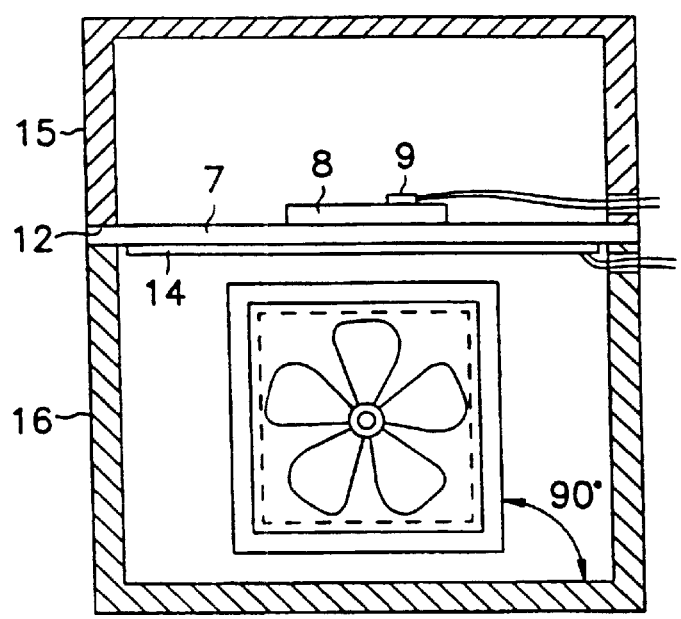
FIG. 4 illustrates a fan mounting arrangement in which the impeller blades of the fan 17 are at an angle, i.e., perpendicular, to the ceramic sample plate 7. Air is drawn into the lower compartment, diverted 90°, driven against the heater, and out of the lower compartment through vents (not shown) on the sidewalls.

FIG. 4 illustrates an alternative embodiment in which the fan 17 assembly is placed at an angle to the heating means 14.

Figure 5:
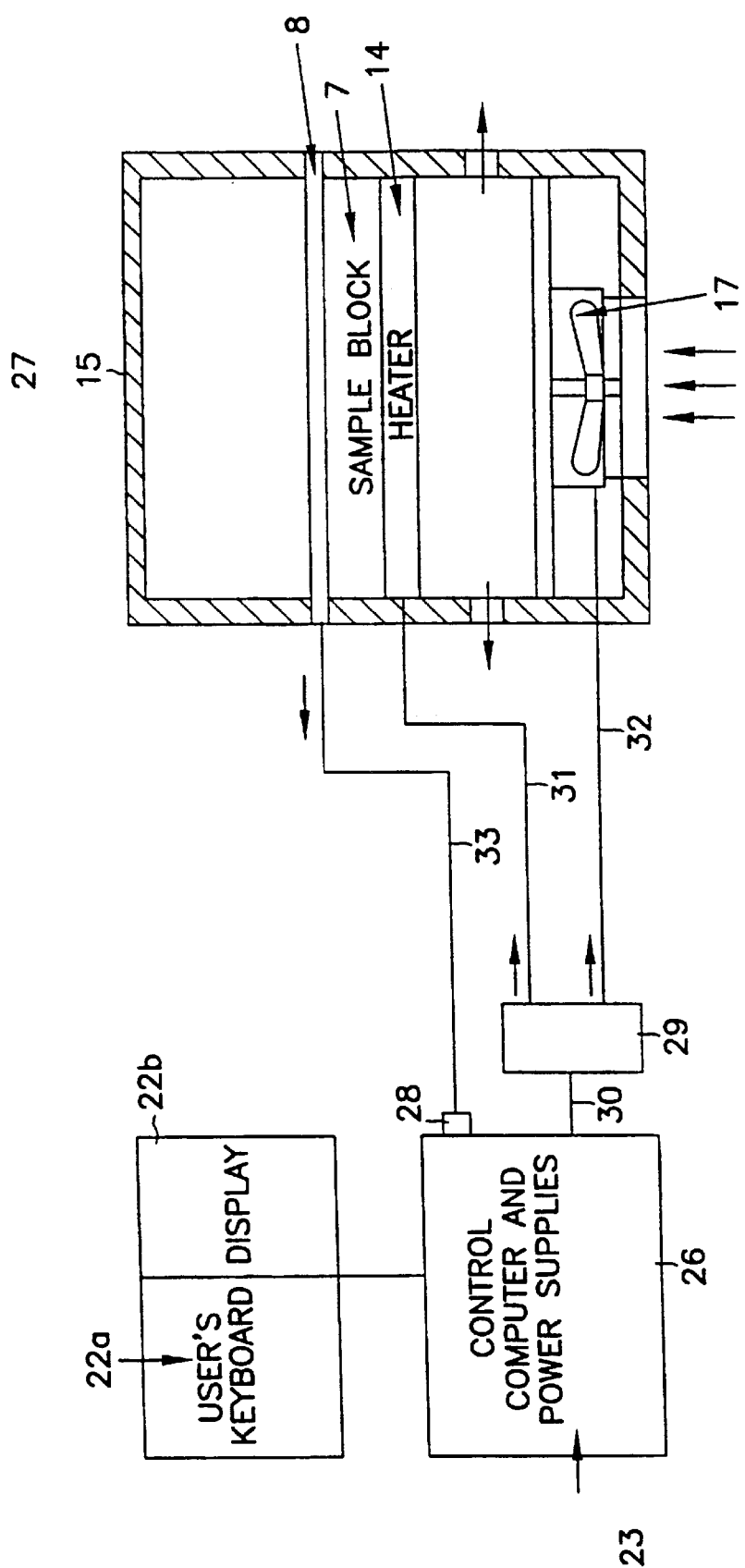
FIG. 5 is a block diagram of the thermal cycler of the invention. Shown are the thermal cycling device 27, a user's keyboard and display 22a and 16b, and a computer 23/power supply 26. Also shown are the control for cooling 32, control for heating 31, an analog to digital converter 28, a cable 30 and a connector 33.

FIG. 5 is a block diagram of the invention. A microcomputer or microprocessor 23 can be programmed by means of input keys 16a and display 16b to cause the substantially flat substrate on the ceramic sample plate 7 to be cycled through a series of temperatures over a predetermined period of time. Although not specifically illustrated in the drawings, it is contemplated that the device of the invention would include, as appropriate, timing mechanisms, electronic or otherwise, for maintaining time intervals for each cycle, and for counting the number of repetitions.

The microcomputer or microprocessor 23 is electrically attached to a relay controller 29 by means of a transmission cable 30. This controller 29 regulates the supply of power 20 to the heating means 14. It also regulates the supply of power 21 to the fan blower motor (not shown). A preferred controller is available from JBR Electronic Systems, Inc. (Baltimore, Md.; ECP2). The cable also supplies power to the blower motor (not shown), and to the heating means 14.

The microcomputer or microprocessor 23 also is connected to an electronic sensing device which is an analog to digital converter 28 that is connected to the temperature sensor 9. A preferred converter 28 is the DAS-TEMP, available from Keithley Metrabyte (Taunton, Mass.). The microcomputer or microprocessor 23 can be any well-known type of temperature controller unit which is programmable to control the heating means 14 and fan motor so as to achieve predetermined temperatures as a function of time on the substantially flat substrates present on the ceramic sample plate 7.

Figure 6:
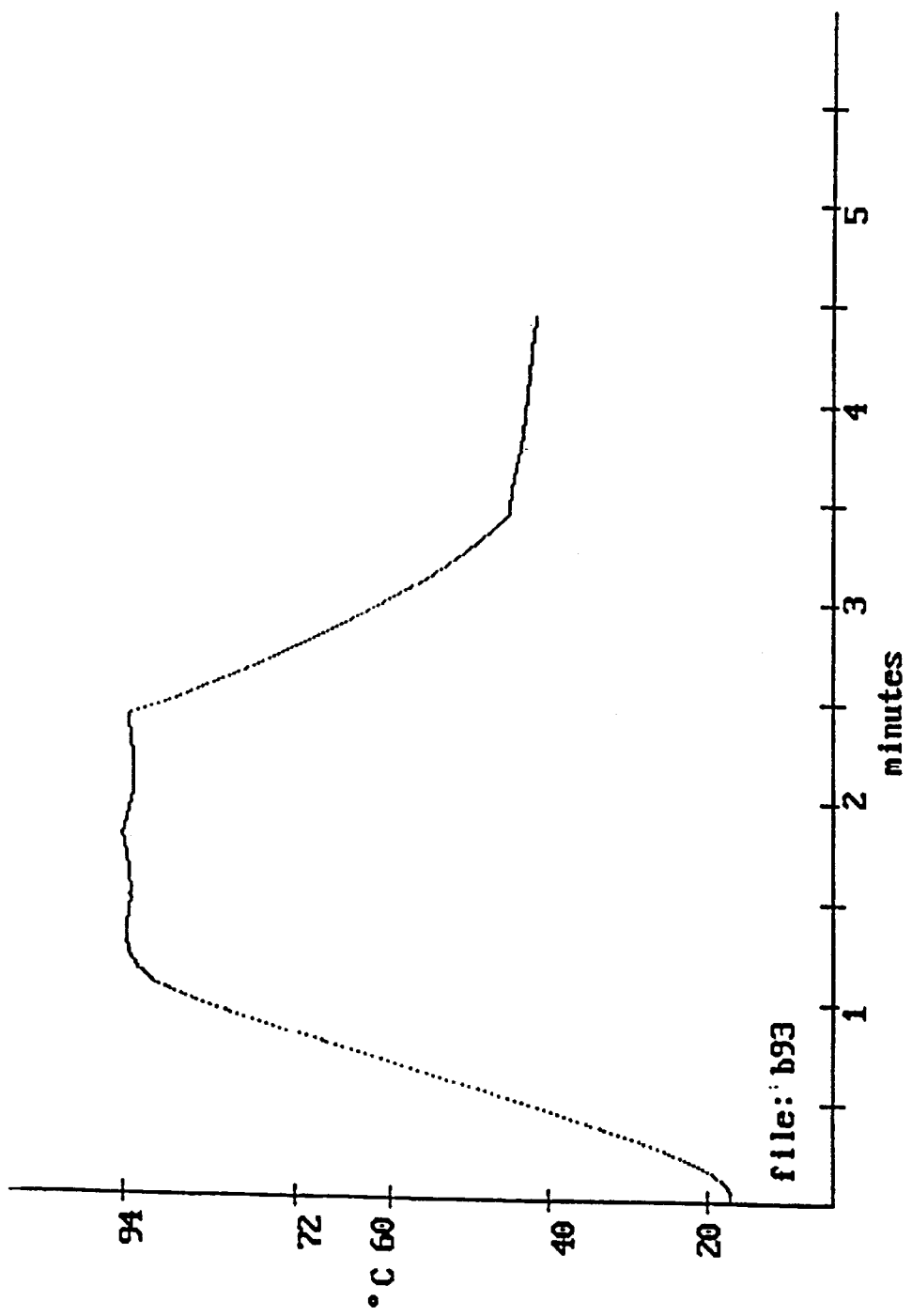
FIG. 6 is a graph of time versus temperature for a representative slide. The slide was heated to 93.6° C., maintained at that temperature for 60 seconds, cooled by active convection for 60 seconds, and then cooled by passive convection for 60 seconds. The plot reveals that the temperature of the representative slide increases at a rate >1° C./second, maintained within 0.5° C. of the target temperature, cooled at a rate >0.7° C./second by active convection, and then cooled at a rate <0.20° C./second by passive convection.

When the device of the present invention is used for cyclic DNA amplification, repetitive cycling through a temperature versus time profile is required. Samples containing a reaction mixture for the polymerase chain reaction generally must be cycled approximately 30–40 times through a temperature versus time profile which corresponds to the denaturation, annealing and elongation phases of the amplification process. FIG. 6 illustrates, in graphic form, the temperature profile of a microscope slide undergoing thermal cycling. It can be seen that the slide reached a temperature of approximately 94° C. on the hot cycle, and then was rapidly cooled down to about 44° C. by active convection on the cold cycle. It can be seen that active convection, relative to passive convection, has a substantially more rapid rate of decrease of temperature on the cold cycle. As a result of use of the present invention, it is possible to realize temperature increases of the flat substrate of at least about 1.0° C./sec or greater, and temperature decreases of the flat substrate of at least about 0.7° C./sec or greater.

Method of the Invention

To amplify nucleic acid sequences in a biological sample, such as a histochemical section or cytochemical smear attached to a microscope slide, the section or smear on the microscope slide is preferably covered with about 5 to 25 μl, more preferably about 5 to 10 μl, of a PCR reagent mixture. Preferably, the PCR reagent mixture lacks at least one reagent, such as enzyme. Then a plastic cover slip is placed over the preparation, the microscope slide is placed on a ceramic thermal cycler sample plate. After the sample plate is brought to about 80° C. and held at that temperature, the cover slip is lifted and 2 to 10 μl of PCR buffer containing the missing reagent(s) are distributed across the surface of the reagent mixture. The cover slip is replaced, and the slide is covered with enough mineral oil to assure that the cover slip, including their edges, is protected from the atmosphere. Preferably, the oil has been preheated, so that its addition does not transiently reduce the temperature of the in situ PCR preparation. Then a standard two-temperature or three-temperature thermal cycle is run for about 40 cycles. Cycle parameters, e.g., number of cycles, and PCR reagent concentrations are optimized by methods well known to the art.

After amplification, the mineral oil is removed from the slide with an organic solvent such as xylene, and the slides are dried with 100% ethanol or a graded series of ethanol concentration. The oil-free preparation is incubated for approximately 15 minutes at about 50° C. in 0.15 M NaCl, 0.015 M Na citrate, pH 7.0 to remove unreacted PCR reagents.

The detection phase of in situ PCR employs two basic detection strategies. The first strategy involves tagging either the PCR primers or at least one of the dNTPs with a radioisotope or with a binding moiety such as biotin, digoxigenin, or flus or with another fluorophore. In this case, tag incorporated into amplified nucleic acid can be analyzed directly, provided that the unreacted tagged reagent has been washed out post-PCR and provided that the washing and drying procedure has not mobilized the amplified nucleic acid from its point of synthesis. The analytical validity of this simple detection strategy requires that the invention has increased in situ PCR specificity sufficiently that negligible nonspecific products have been made which are large enough to resist washing from the preparation.

To test and validate this consequence of the first three aspects of the invention, appropriate control reactions can be performed. The logically most compelling control reaction is to perform the procedure on cells known to lack the target sequence; validation of the simplified detection strategy requires that no signal be generated in the control cells. Often such control cells are present in a histochemical or cytochemical preparation, so that the standard analysis contains its own control. A less compelling control is to use primers which differ sufficiently from the optimal primers for the target sequence that they will not amplify the target sequence under the specified annealing and extension conditions.

The second strategy involves detecting amplified nucleic acid by in situ hybridization to a tagged nucleic acid probe: an oligonucleotide or polynucleotide with a sequence complementary to at least part of the amplified nucleic acid sequences (preferably excluding the primer sequences). In situ hybridization, well known in the histochemical and cytochemical art, has four basic steps: denaturation of DNA in the test sample, annealing of probe to test sample nucleic acid under stringent conditions, wash of the microscope slide with a solvent under stringent conditions to remove unhybridized probe, and detection of the probe which has been retained on the slide.

Regardless of which detection strategy is used, the methods for observing and recording the presence and location of tag on the microscope slide are the same. If the tag is a radioisotope (preferably a strong beta radiation-emitter, such as $^{32}$P or $^{125}$I), the microscope slide is coated with nuclear track emulsion such as NTB-2 from Eastman Kodak Co. (Rochester, N.Y.), incubated at 4° C. for an interval determined by trial and error, and developed by standard methods to leave microscopically detectable silver grains in the vicinity of immobilized tags. Procedures for $^{125}$I tagging probe or PCR product are described by Haase et al., *Proc. Nat. Acad. Sci USA*, 87, 4971 (1990), incorporated herein by reference.

If the tag is a fluorophore, it may be observed directly in a fluorescence microscope with excitation and emission filters optimized for the particular fluorophore. This detection method is particularly suitable for multiplex in situ PCR with different primer pairs for different target nucleic acid sequences. Either different fluorophores can be attached to primers of different specificity, or different fluorophores can be attached to probes of different specificity. Methods of attaching fluorophores to oligonucleotides and polynucleotides, preferably at their 5' ends, are well known in the nucleic acid chemistry and PCR arts.

If the tag is a binding moiety such as biotin or digoxigenin, it is incorporated directly into PCR product (via primers or dNTPs) or into probes by essentially the same methods used to attach other tags. However, in this case, signal generation requires additional detection steps.

Preferably, the microscope slide is incubated in buffered aqueous solvent containing a covalent conjugate of a detection enzyme and a binding protein specific for the tag (avidin or streptavidin for biotin, an anti-digoxigenin antibody for digoxigenin, an anti-fluorescein antibody for fluorescein). The preferred detection enzyme is horseradish peroxidase or alkaline phosphatase. After unbound enzyme conjugate is removed by washing in a buffered aqueous solvent, the microscope slide is immersed in a solution containing a chromogenic substrate for the enzyme used. After an insoluble dye, product of the enzyme reaction, has been deposited at points on the microscope slide where enzyme conjugate has been bound, unreacted substrate is washed away in water or buffered aqueous solvent to prevent the buildup of nonspecific background stain over time. The preferred chromogenic substrates which generate insoluble products are well known in the histochemical and cytochemical art, as are the methods for staining and for enzyme conjugate incubation and washing. The substrates and enzyme conjugates are commercially available from a wide variety of sources well known to histochemists and cytochemists.

A preferred companion procedure in the detection steps of the present invention is counterstaining of the microscope slide with fluorescent dyes (for fluorescent tags) or chromophoric dyes (for radio-autoradiographic detection or enzymatic generation of insoluble chromophores) which emit or absorb with different spectral characteristics than the analyte-specific signals and which highlight cell structures, especially in cells which lack target nucleic acid sequence. Especially preferred for examination of insoluble blue dye deposits by transmission microscopy is counterstaining by nuclear fast red, standard in the histochemical and cytochemical art. The methods for examining stained in situ PCR preparations by transmission or fluorescence microscopy are well known in the histochemical and cytochemical art, as are methods of recording permanently the microscopic image photographically or via digitized video images.

The invention will be further described by the following examples.

EXAMPLE 1

A thermal cycler of the invention 27 may include the following components. The housing, comprising a lid 15 and a lower hollow compartment 16, is constructed from polystyrene, polypropylene, polyethylene or other plastics having appropriate thermal and electrical conductances. The ceramic alumina plate 1 is about 6.5" long, about 3.5" wide, and about 0.025" thick. The microscope slides are about 3.0" long, about 1.0" wide, and about 0.125" thick. The heater 14 is of the etched foil type, and is electrically insulated with a thin film of Kapton or similar substance. The fan 17 may be powered by alternating current or direct current. The impeller blades of the fan may be constructed from plastic or metal.

The fan 17 and the heater 14 arm controlled by electrical switches of the relay type. The relays can be of the solid state or mechanical varieties.

The computer or controller 23 can be a commercial microcomputer or a self-contained microprocessor. A microprocessor can be incorporated into the control electronics of the apparatus by methods well known to the art. The microprocessor executes commands written in software that collect user input via the keyboard, compare the input to actual temperatures, and turn off or on the heating 8 or cooling 11 units as appropriate. The electronics may also include a timer, readable by the microprocessor. This allows the microprocessor to compare the elapsed time that the reaction mixture has been at a particular temperate and compare it to a desired time input by the user.

The temperature sensor 9 can be of the thermocouple type, or the thermistor type, or the resistance temperature detector type, or the current detector type. In each of these devices a change in temperature at the interface between the sensor and its environment produces a change in the ability of the sensor to conduct electrical current. The sensors generate electrical signals that are proportional to the extent of the temperature change. The temperatures of the experimental slides 10 are taken by the thermosensor 9 as the temperature of the representative slide 2. A representative time versus temperature plot for the thermal cycler described above is shown in FIG. 6. The difference between the rates of active and passive convection illustrates that a cooling means, e.g., a fan, is required for the effective performance of the invention.

Communication between the computer 23 and the temperature sensor 9 is maintained by an electrical device known as an analog to digital converter. This device takes the electrical signal produced by the temperature sensor and converts it to a form that the circuitry of the computer can evaluate. Different types of temperature sensors require different specialized types of analog to digital converters.

Communication between the computer 23 and the relays is maintained by switching devices. These devices respond to signals from the computer by producing an altered electrical signal that causes a response in the relay.

The computer program, implemented in a combination of assembly language and the C language, although other programming languages may be used, causes the computer 23 to evaluate the temperature received from the temperature sensor 9, compare this value to the "target" temperate and send appropriate electrical signals to the relays controlling the heater 14 and the fan 17. Specific patterns of signals from computer 23 to relays provide the means by which the representative slide is heated, cooled, or maintained at a steady temperature.

EXAMPLE 2

Cells of the stable human cervical cancer cell line, SiHa (ATCC HTB 35), containing one integrated copy of human papilloma virus (HPB) type 16 genome per human genome, are grown to density of about $10^5$ cells/mL in Eagle's minimal essential medium with non-essential amino acids, sodium pyruvate, and 15% fetal bovine serum, washed two times in Tris-buffered saline, adjusted to an approximate density of $10^4$ cells/mL, and stirred overnight at room temperature in 10% (vol/vol) formaldehyde in phosphate buffer. The formaldehyde-fixed cells are centrifuged at 2,000 rpm for 3 minutes, and the pellet is embedded in paraffin. Microtome sections (4 μm thickness) of the paraffin block are attached to glass microscope slides which had been dipped in 2% 3-aminopropyltriethoxysilane (Aldrich Chemical Co.) in acetone by floating the sections in a water bath.

After attachment, sections are deparaffinized and proteolytically digested with reagents from the Viratype® in situ Tissue Hybridization Kit (Life Technologies, Inc., Gaithersburg, Md.) following the manufacturer's instructions. Slides are overlaid with 5 to 10 µl of PCR solution (see below). A plastic cover slip is placed over each in situ PCR preparation. The cover slip is anchored to the slide with a drop of nail polish The slide is placed on the sample plate 7 of the thermal cycler described in Example 1, and covered with approximately 1 ml of mineral oil.

The pH 8.3 PCR solution contains 10 mM TrisCl, 50 mM KCl, 4.5 mM $MgCl_2$, 20 mM of each dNTP, 0.2 unit/µl of AmpliTaq® DNA polymerase (Perkin Elmer Cetus Instruments, Norwalk, Conn.), and 6 µM of each primer. The primers employed are PV1, PV2, PV3, PV4, PV5, PV6 and PV7 (see U.S. Pat. No. 5; PV1 5' CAGGACCCACAG-GAGCGACC 3' (SEQ ID NO:1); PV2 5' TTA-CAGCTGGGTTTCTCTAC 3' (SEQ ID NO:2); PV3 5' CCGGTCG ATGTATGTCTTGT 3' (SEQ ID NO:3); PV4 5' ATCCCCTGTTTTTTTTTCCA 3' (SEQ ID NO:4); PV5 5' GGTACGGGATGTAATGGATG 3' (SEQ ID NO:5); PV6 5' CCACTTCCACCACTATACTG 3' (SEQ ID NO:6); PV7 5' AGGTAGAAGGGCGCCATGAG 3' (SEQ ID NO:7)) which result in the production of overlapping approximately 450 bp PCR products. The predicted PCR product is a 1247 bp product.

For the first thermal cycle, denaturation is performed for 3 minutes at 94° C., and annealing/extension are performed for 2 minutes at 55° C.; the remaining 39 cycles consist of 1 minute denaturation at 94° C. and 2 minutes annealing-extension.

After DNA amplification, mineral oil is removed by dipping in xylene, the cover slip is removed, and the mounted sections are dried in 100% ethanol. Each slide is incubated with 10 µl of a 500 ng/ml solution of biotinylated HPV type 16 specific polynucleotide probe (Viratype Kit, Life Technologies, Inc.) in 0.03 M Na citrate, 0.30 M NaCl, pH 7.0, 5% dextran sulfate, 50% formamide at 100° C. for 5 minutes and then 37° C. for 2 hours; then the slide is treated with an alkaline phosphatase-streptavidin conjugate and the phosphatase substrates, 5-bromo-4-chloro-3-indolyl phosphate (BCIP) and nitro blue tetrazolium (NBT), according to the instructions of the supplier of the S6800 Staining Kit (Oncor, Gaithersburg, Md.). After enzymatic detection of biotinylated probe captured on the sections, the sections are counterstained with nuclear fast red for 5 minutes.

When the stained slides are examined by mission microscopy under 40–400× magnification, single-copy HPV targets in SiHa cells are detectable in most nuclei.

All publications and patents are incorporated by reference herein, as though individually incorporated by reference, as long as they are not inconsistent with the present disclosure. The invention is not limited to the exact details shown and described, for it should be understood that many variations and modifications may be made while remaining within the spirit and scope of the invention defined by the claims.

What is claimed is:

1. A device for subjecting a plurality of biological samples disposed on at least one substantially flat substrate to thermal cycling, comprising:

a thermal sensing means placed on the surface of one substantially flat substrate and at least one substantially flat substrate lacking said thermal sensing means and comprising at least one biological sample;

a means for holding the plurality of substantially flat substrates, wherein the means for holding comprises a ceramic sample plate, and wherein the substantially flat substrates are disposed on the surface of said holding means;

a means for heating the lower surface of the means for holding, wherein the means for heating is positioned in close proximity to the means for holding, and wherein the means for heating comprises a plate which is parallel to the ceramic plate;

a means for cooling the surface of the means for heating, wherein the means for cooling comprises a rotating means for dispersing air; and a means for controlling, wherein the controlling means is operatively connected to the means for thermal sensing, the means for heating and the means for cooling such that the temperature of the substrates can be rapidly and controllably increased and decreased by the control means in response to the temperature sensed by the means for sensing such that the biological sample can be subjected to rapid thermal cycling over a temperature range of at least 40° C.

2. A thermal cycling device useful for the amplification of nucleic acids, comprising:

a thermal sensing means placed on the surface of one substantially flat substrate and at least one substantially flat substrate lacking said thermal sensing means and comprising at least one biological sample;

a means for holding the plurality of substantially flat substrates, wherein the means for holding comprises an alumina sample plate, and wherein the substantially flat substrates are disposed on the surface of said holding means;

a means for heating the surface of the means for holding, wherein the means for heating is attached to the means for holding, and wherein the means for heating comprises a plate which is parallel to the alumina plate;

a means for cooling the surface of the means for heating, wherein the means for cooling comprises a rotating means for dispersing air; and a means for controlling, wherein the controlling means is operatively connected to the means for thermal sensing, the means for heating and the means for cooling such that the temperature of the substrates can be rapidly and controllably increased and decreased by the control means in response to the temperature sensed by the means for sensing such that the biological sample can be subjected to rapid thermal cycling over a temperature range of at least 30° C.

3. A device for maintaining the temperature of a plurality of biological samples which are disposed on at least one substantially flat substrate, comprising:

a thermal sensing means placed on the surface of one substantially flat substrate and at least one substantially flat substrate lacking said thermal sensing means and comprising at least one biological sample;

a means for holding the plurality of substantially flat substrates, wherein the means for holding comprises a ceramic sample plate, and wherein the substantially flat substrates are disposed on the surface of said holding means;

a means for heating the surface of the means for holding, wherein the means for heating is positioned in close proximity to the means for holding, wherein the means for heating comprises a plate which is parallel to the alumina plate;

a means for cooling the surface of the means for heating, wherein the means for cooling comprises a rotating means for dispersing air; and a means for controlling, wherein the controlling means is operatively connected to the means for thermal sensing, the means for heating and the means for cooling such that the temperature of the substrates can be maintained at a particular temperature by the control means in response to the temperature sensed by the means for sensing such that the biological sample can be maintained at a particular temperature over a temperature range of at least 40° C.

4. A device useful for the in situ hybridization of nucleic acids, comprising:

a thermal sensing means placed on the surface of one substantially flat substrate and at least one substantially flat substrate lacking said thermal sensing means and comprising at least one biological sample;

a means for holding the plurality of substantially flat substrates, wherein the means for holding comprises an alumina sample plate, and wherein the substantially flat substrates are disposed on the surface of said holding means;

a means for heating the lower surface of the means for holding, wherein the means for heating is attached to the means for holding, wherein the means for heating is positioned in close proximity to the means for holding, and wherein the means for heating comprises a plate which is parallel to the alumina plate;

a means for cooling the lower surface of the means for heating, wherein the means for cooling comprises a rotating means for dispersing air; and a means for controlling, wherein the controlling means is operatively connected to the means for thermal sensing, the means for heating and the means for cooling such that the temperature of the substrates can be maintained at a particular temperature by the control means in response to the temperature sensed by the means for sensing such that the biological sample can be maintained at a particular temperature over a temperature range of at least 30° C.

5. The device of claim 1, 2, 3 or 4 wherein the means for sensing comprises a thermocouple.

6. The device of claim 1, 2, 3 or 4 wherein the means for sensing comprises a means other than a thermocouple.

7. The device of claim 1, 2, 3 or 4 wherein the flat substrate is a glass microscope slide.

8. The device of claim 1, 2, 3 or 4 wherein the flat substrate comprises glass, plastic, nitrocellulose or nylon.

9. The device of claim 1 or 3 wherein the ceramic is alumina.

10. The device of claim 1 or 3 wherein the ceramic is other than alumina.

11. The device of claim 1, 2, 3 or 4 wherein the eating means is an etched foil heater.

12. The device of claim 1, 2, 3 or 4 further comprising a housing containing the means for holding, the means for cooling, the means for heating, and the means for sensing.

13. The device of claim 1 or 3 wherein the space which separates the ceramic plate from the parallel plate is less than about 1/8 of an inch.

14. The device of claim 1, 2, 3 or 4 wherein the parallel plate is formed from a conductive material.

15. The device of claim 14 wherein the material is ceramic, aluminum or copper.

16. A method for amplifying target nucleic acid comprising:

(a) contacting a biological sample, which comprises nucleic acid, that is disposed on a substantially flat substrate with an amount of PCR reagents so as to yield a mixture;

(b) subjecting the mixture to thermal cycling in the device of claim 1 or 2 so as to yield amplified nucleic acid.

17. A method for maintaining the temperature of a biological sample disposed on a substantially flat substrate, comprising contacting the substrate with the device of claim 1, 2, 3 or 4 so as to maintain the temperature of the biological sample on said substrate.

18. A method for in situ PCR amplification of target nucleic acid wherein said amplified nucleic acid is spatially confined to individual cells originally containing said target nucleic acid, comprising:

(a) contacting fixed cells suspected of containing the target nucleic acid with an amount of PCR reagents sufficient to amplify said target nucleic acid so as to form a mixture; and (b) subjecting the mixture to thermal cycling in the device of claim 1 or 3 so as to yield amplified nucleic acid.

19. A method for in situ hybridization of a target nucleic acid wherein said target nucleic acid is spatially confined to a substantially flat surface, comprising:

(a) contacting the target nucleic acid with an amount of a labeled probe comprising a preselected DNA comprising the target nucleic acid sequence to as to form a mixture;

(b) maintaining the temperature of the mixture for a sufficient time to form binary complexes between at least a portion of said probe and said target nucleic acid, wherein the temperature is maintained on the device of claim 3 or 4; and (c) detecting the absence or presence of said binary complexes.

20. A method for in situ hybridization of target nucleic acid wherein said target nucleic acid is spatially confined to individual cells originally containing said target nucleic acid, comprising:

(a) contacting fixed cells suspected of containing the target nucleic acid with with an amount of a labeled probe comprising a preselected DNA comprising the target nucleic acid sequence so as to form a mixture; and (b) maintaining the temperate of the mixture for a sufficient time to form binary complexes between at least a portion of said probe and said target nucleic acid, wherein the temperature is mainlined on the device of claim 3 or 4; and (c) detecting the absence or presence of said binary complexes.

21. The method of claim 16 or 17 wherein said biological sample comprises cells which have been exposed to a fixative.

22. The method of claim 16 or 17 wherein said biological sample is a tissue section.

23. The method of claim 22 wherein the tissue section was previously incubated with antibodies comprising a detectable label.

24. The method of claim 20 wherein a tissue section provides the cells.

25. The method of claim 24 wherein the tissue section was previously incubated with antibodies comprising a detectable label.

26. The method of claim 16, 17 or 18 further comprising:

c) detecting said amplified nucleic acid.

27. A device for subjecting a biological sample to thermal cycling comprising:

a housing;

a flat substrate having a thermal sensor coupled to said flat substrate, said flat substrate having a biological sample disposed thereon;

a holder for said flat substrate, said holder attached to said housing, wherein said holder comprises a ceramic sample plate which is parallel to a second plate, wherein the sample plate and the second plate are separated by no more than about $1/8$ of an inch, and wherein said flat substrate is disposed on the surface of said ceramic sample plate;

a cooler for said flat substrate, said cooler attached to said housing; and a heater thermally coupled to the second plate.

28. A device for maintaining the temperature of a biological sample comprising:

a housing;

a flat substrate having a thermal sensor coupled to said flat substrate, said flat substrate having a biological sample disposed thereon;

a holder for said flat substrate, said holder attached to said housing, wherein said holder comprises a ceramic sample plate which is parallel to a second plate, wherein the sample plate and the second plate are separated by no more than about $1/8$ of an inch, and wherein said flat substrate is disposed on the surface of said ceramic sample plate;

a cooler for said flat substrate, said cooler attached to said housing; and a heater thermally coupled to the second plate.

29. The device of claim 27 or 28 wherein said holder holds a plurality of flat substrates.

30. The device of claim 27 or 28 wherein said cooler is a fan.

31. The device of claim 27 or 28 further comprising:

a controller operatively connected to the thermal sensor, the heater and the cooler such that the temperature of the flat substrate can be controllably increased and decreased by the controller in response to the temperature sensed by the means for thermal sensor.

32. The device of claim 27 or 28 wherein the biological sample can be subjected to rapid thermal cycling over a temperature range of at least 40° C.

33. The device of claim 2 or 4 wherein the space which separates the alumina plate from the parallel plate is less than about $1/8$ of an inch.

* * * * *

UNITED STATES PATENT AND TRADEMARK OFFICE
CERTIFICATE OF CORRECTION

PATENT NO.    : 6,228,634 B1
DATED         : May 8, 2001
INVENTOR(S)   : Jonathan Chaplin and Martin Blumenfeld It is certified that error appears in the above-identified patent and that said Letters Patent is hereby corrected as shown below:

<u>Column 25,</u>
Line 56, please delete "eating" and insert -- heating -- therefor.

<u>Column 26,</u>
Line 30, please delete first occurance of "to" and insert -- so -- therefor.
Line 44, please delete first occurance of "with".
Line 51, please delete "mainlined" and insert -- maintained -- therefor.

Signed and Sealed this

Twenty-first Day of May, 2002

Attest:

Attesting Officer

JAMES E. ROGAN
Director of the United States Patent and Trademark Office